United States Patent
Theis et al.

[11] Patent Number: 5,171,235
[45] Date of Patent: Dec. 15, 1992

[54] TAMPON AND MANUFACTURE THEREOF

[75] Inventors: Dirk Theis, Kelheim; Walter Fester, Saal, both of Fed. Rep. of Germany

[73] Assignee: Hoechst Aktiengesellschaft, Fed. Rep. of Germany

[21] Appl. No.: 678,665

[22] Filed: Apr. 1, 1991

[30] Foreign Application Priority Data

Apr. 3, 1990 [DE] Fed. Rep. of Germany ....... 4010700

[51] Int. Cl.⁵ .............................................. A61F 13/15
[52] U.S. Cl. .................................. 604/358; 604/374; 604/385.1; 604/904
[58] Field of Search ............ 604/904, 374, 378, 385.1, 604/358, 363, 384, 375, 285–288, 368, 370

[56] References Cited

U.S. PATENT DOCUMENTS

| | | | |
|---|---|---|---|
| 810,139 | 1/1906 | Green | 604/374 |
| 2,099,931 | 11/1937 | Fourness | 604/904 |
| 2,207,030 | 12/1941 | Hill | 604/904 |
| 2,264,586 | 12/1941 | Ross | 604/374 |
| 2,286,817 | 6/1942 | Knight | 604/904 |
| 2,328,795 | 9/1943 | Finks | 604/904 |
| 3,156,016 | 11/1964 | Dunlap et al. | |
| 3,359,981 | 12/1967 | Hoechstrasser | 604/374 |
| 4,169,121 | 9/1979 | Pietsch et al. | 604/376 |
| 4,627,849 | 12/1986 | Walton et al. | |
| 4,699,618 | 10/1987 | Sustmann | 604/365 |
| 5,041,104 | 8/1991 | Seal | 604/367 |

FOREIGN PATENT DOCUMENTS

| | | | |
|---|---|---|---|
| 113374 | 3/1969 | Denmark | 604/374 |
| 1435417 | 10/1968 | Fed. Rep. of Germany | |
| 2094637 | 9/1982 | United Kingdom | 604/904 |

Primary Examiner—Randall L. Green
Assistant Examiner—K. Reichle
Attorney, Agent, or Firm—Connolly & Hutz

[57] ABSTRACT

There is described a tampon made of continuous filaments based on a man-made fiber tow with a water-holding capacity of at least 1000% by weight, the tampon consisting essentially of continuous filaments in a perpendicular arrangement relative to the longitudinal axis of the tampon with essentially only one free filament end at the surface per filament while the other free filament end is on the inside.

7 Claims, 1 Drawing Sheet

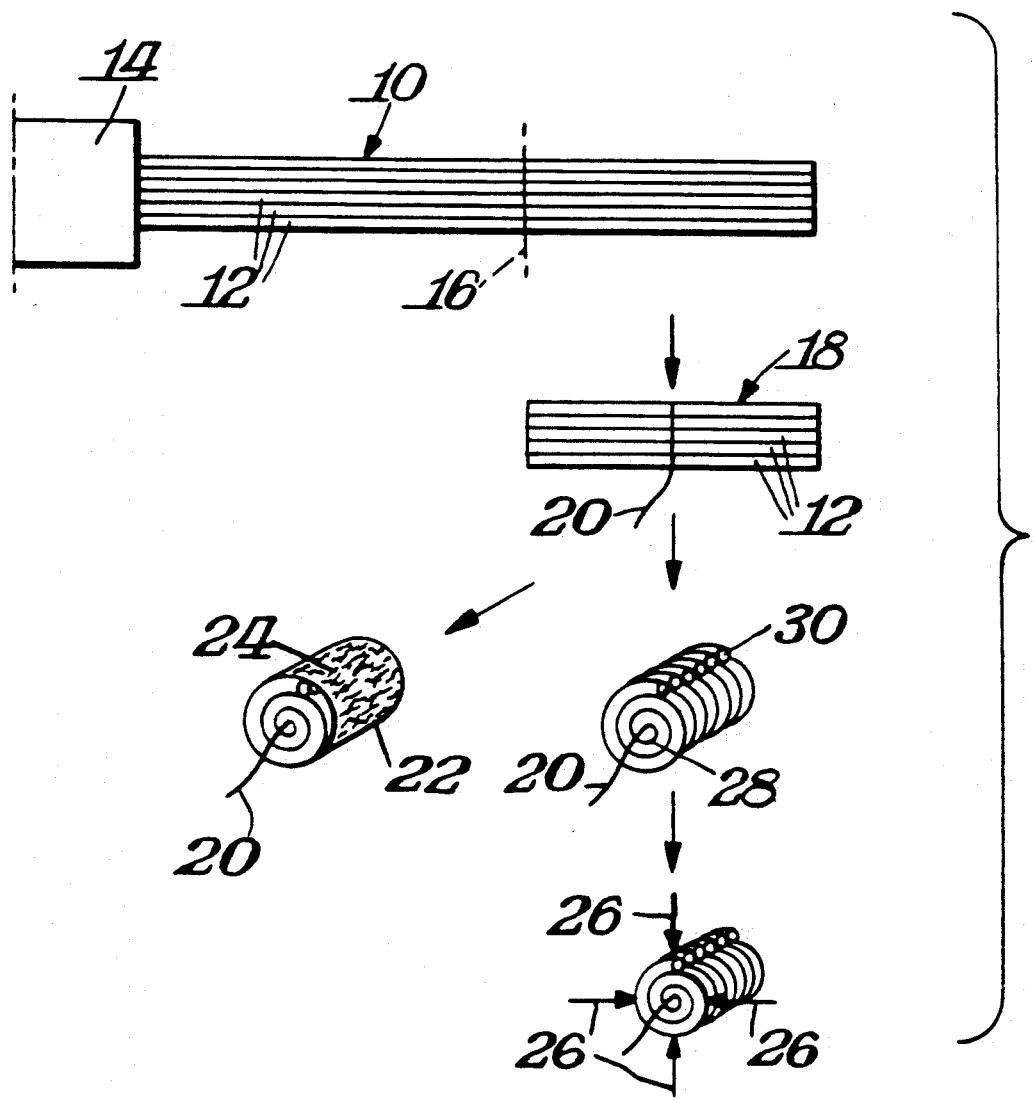

TAMPON AND MANUFACTURE THEREOF

DESCRIPTION

The present invention relates to a tampon made of continuous filaments and to a process for manufacturing it. Tampons are customarily made of webs, in particular card webs. They generally comprise cellulosic fibers.

U.S. Pat. No. 4,627,849 discloses tampons whose defining feature is the imposition of a so-called "microwaviness". This is to be understood as meaning an arrangement of crimped individual filaments in which the curved portions of a plurality of filaments are grouped together so as to confer waviness on the fiber mats used as a whole. From FIG. 10a of this patent it is possible to discern an embodiment for a tampon whose filaments preferentially extend in the longitudinal direction of the tampon axis. However, such a tampon is costly to manufacture. For instance, continuous manufacture is not possible. The patent in question also proposes the use of continuous fiber tows (hereinafter referred to as tows), but this possibility is not further embodied therein.

It has now been found that tampons can be manufactured from tows in a simple manner. This process does away with the textile pretreatment steps which were necessary with the use of card webs and enables manufacture to be continuous. Furthermore, the product obtained has virtually no free filament ends along the shell surface of the tampon. Such free filament ends can lead to skin irritation and allergic reactions and therefore are undesirable on the surface of a tampon.

The single FIGURE of drawing illustrates the tampon of the present invention and its manufacture.

The fiber material used for the purposes of the present invention must have a water-holding capacity (as defined in German Standard Specification DIN 61640) of at least 1000% by weight, i.e. it must at least be able to hold an amount of water which corresponds to at least ten times its own weight. Customarily, the water-holding capacity is 1000-2000% by weight, but preferably it is at least 1500% by weight.

The fiber material can be cellulose, preferably unmodified cellulose. Examples thereof are cellulose spun by the direct solution process, for example from N-methyl-morpholine N-oxide as solvent, and regenerated cellulose, such as cuprammonium rayon or in particular viscose rayon.

The tow used has a linear density of about 5 to 50 ktex, in particular of about 10 to 40 ktex. The choice of the tow linear density depends essentially on the desired dimensions of the end product.

The linear density of the individual filaments of the tow to be used is customarily between about 1 and 10 dtex, in particular of about 2 to 5 dtex. The choice of this parameter is limited at the upper end by the necessary mechanical strength of the tampon, while the lower limit is chiefly determined by the economics of the fibermaking process.

The tow to be used must be crimped in order to confer sufficient strength on the end product. It is possible to employ any kind of customary crimping, such as gear crimping and in particular stuffer box crimping. Especially in the case of viscose filaments the crimping due to the viscose process can be sufficient without further mechanical treatment.

Essential features of the tampon of the present invention are the construction from continuous filaments, essentially perpendicular arrangement of these filaments relative to the longitudinal axis of the tampon and the incorporation of half the free filament ends on the inside of the tampon. This makes it possible that only half the free filament ends of the tow appear on the shell surface of the cylinder, so that the cylinder surface which later comes into contact with the skin contains only a low level of such free filament ends.

The tampon of the present invention can be manufactured directly from the tow material or it can be additionally provided with a wrapping fleece.

Such wrapping fleeces are known per se. They comprise for example ultralightweight fleeces based on polyester/polyethylene bicomponent fibers. The basis weight of such wrapping fleeces is preferably less than or equal to 15 g/m$^2$, particularly preferably about 10 g/m$^2$.

The tampon of the present invention can be provided with a recovery string.

The recovery string can be a folded or single yarn made of natural and/or synthetic fibers. The folded or single yarn used in particular is made of a thermoplastic polymer which, after introduction into the tampon, can be adhered to the surrounding filaments, for example by heating to above the softening point of the thermoplastic polymer.

In manufacturing the tampon of the present invention, the tow is cut into trapezoidal or in particular into rectangular pieces. The longitudinal edges of these pieces are about 5 to 30 cm in length, in particular about 10 to 20 cm. The length of these edges together with the tow thickness is the chief determinant of the diameter of the tampon of the present invention. The width of the trapezoidal or rectangular piece cut from the tow chiefly determines the length of the tampon.

Preferably the width is between 2 and 6 cm. Before being cut to size the tow may if necessary be fanned out in order to uniformize the arrangement of the individual filaments. The fanning out may be effected in a conventional manner either mechanically or by jets of fluid, as described for example in U.S. Pat. No. 3,156,016 or German Patent No. 1,435,417.

After the tow has been cut to size either the tampon can be rolled up at once or a recovery string is introduced first. This is done by placing, adhering or fastening a recovery string approximately in the middle of the long edge of the rectangular tow section, so that the string extends essentially perpendicularly to the position of the individual filaments.

In a particularly preferred embodiment of the process of the present invention, the recovery string is attached at this point by looping the tow section with the string and leaving a free end of the string to extend beyond one side of the tow section for use as a recovery string.

After the tow section has been cut to size and any recovery string has been introduced, the tow section is rolled up, starting at a short end of the tow section, so that the free filament ends at this end come to be situated on the inside of the tampon. Only the free filament ends of the other short end of the tow section will later be situated on the surface of the tampon. These filament ends, depending on the shape of the tow section, extend rectilinearly across the tampon surface either at an inclined angle or preferably in the direction of the longitudinal axis of the tampon.

The rolled-up tow is then pressed by applying a pressure perpendicularly to the cylinder surface.

A suitable apparatus for this purpose is described for example in FIGS. 4, 4a and 4b of U.S. Pat. No. 4,627,849. Before the pressing the tampon may be wrapped with a wrapping fleece. If a recovery string made of a thermoplastic material is used, the tampon may be heated during the pressing in order to adhere the recovery string to the surrounding fibers. This generally requires a temperature above the softening point of the thermoplastic material.

The tampons of the present invention can be used for many purposes, for example for medical purposes or in particular as catamenial devices. They are noteworthy for high absorbency and for particularly good compatibility. More particularly, they are simple and economical to manufacture.

As shown in the single figure of drawing, a longitudinal tow 10 of continuous filaments 12 is provided from a source 14. A cutter 16 is used to remove a piece 18 of predetermined length from the longitudinal two. Prior to rolling of the two piece 18 into a tampon 20, a recovery string 22 may be placed on the piece. A fleece wrapper 24 may be placed over the rolled two piece, as shown. Alternatively, the rolled two piece may be pressed by perpendicular forces 26 in all directions to compact the formed tampon. In the finished tampon, one end 28 of each filament 12 is located interiorly of the tampon while the other end 30 is on the surface of the tampon.

What is claimed is:

1. A tampon comprising a two of continuous filaments of crimped manmade fibers having a water-holding capacity of at least 1000% by weight and a linear density of about 5 to 50 ktex, the individual filaments of the two having a linear density of about 1 to 10 dtex, the tampon having a longitudinal axis and the continuous filaments being arranged perpendicular relative to the longitudinal axis, each filament having opposite free ends with one free end at an outside tampon surface while the other free end is situated inside of the tampon.

2. The tampon of claim 1, wherein the man-made fibers are cellulosic fibers.

3. The tampon of claim 2, wherein the cellulosic fibers are viscose fibers.

4. The tampon of claim 1, wherein the individual filaments have a linear density of about 2 to 5 dtex.

5. The tampon of claim 1, wherein the free filament ends at the outside tampon surface form a line which extends parallel to the longitudinal axis of the tampon.

6. The tampon of claim 1, including a recovery string made of a thermoplastic material secured to the filaments of the tampon.

7. The tampon of claim 1, including a wrapping fleece surrounding the continuous filaments.

* * * * *

UNITED STATES PATENT AND TRADEMARK OFFICE
CERTIFICATE OF CORRECTION

PATENT NO.  :  5,171,235
DATED       :  December 15, 1992
INVENTOR(S) :  Dirk Theis It is certified that error appears in the above-identified patent and that said Letters Patent is hereby corrected as shown below:

Column 3, lines 21, 22, 24, and 25, "two" should read -- tow --.

Claim 1, line 1 (col. 4, line 4, "two" should read -- tow --.

Signed and Sealed this

Nineteenth Day of October, 1993

Attest:

BRUCE LEHMAN

*Attesting Officer*          *Commissioner of Patents and Trademarks*